(12) United States Patent
Kim et al.

(10) Patent No.: US 9,327,225 B2
(45) Date of Patent: May 3, 2016

(54) AIR CLEANING FILTER AND METHOD FOR MANUFACTURING THE SAME

(71) Applicant: LG Electronics Inc., Seoul (KR)

(72) Inventors: Eunjeong Kim, Gyeongsangnam-Do (KR); MinA Son, Gyeongsangnam-Do (KR); Jeongyon Kim, Gyeongsangnam-Do (KR); Myungsuk Lee, Busan (KR)

(73) Assignee: LG Electronics Inc., Seoul (KR)

( * ) Notice: Subject to any disclaimer, the term of this patent is extended or adjusted under 35 U.S.C. 154(b) by 235 days.

(21) Appl. No.: 13/759,105

(22) Filed: Feb. 5, 2013

(65) Prior Publication Data

US 2013/0199234 A1    Aug. 8, 2013

(30) Foreign Application Priority Data

Feb. 6, 2012   (KR) .................. 10-2012-0012005

(51) Int. Cl.
    *B01D 46/00*    (2006.01)
    *A61L 9/16*    (2006.01)

(52) U.S. Cl.
    CPC .............. *B01D 46/0028* (2013.01); *A61L 9/16* (2013.01); *A61L 2209/14* (2013.01); *B01D 2239/0442* (2013.01); *B01D 2239/0478* (2013.01)

(58) Field of Classification Search
    CPC .. A61L 9/16; A61L 2209/14; B01D 46/0028; B01D 2239/0478; B01D 2239/0442
    USPC .............. 62/407, 448, 186, 408, 440; 96/226, 96/227, 135
    See application file for complete search history.

(56) References Cited

U.S. PATENT DOCUMENTS

| | | | |
|---|---|---|---|
| 3,661,628 A * | 5/1972 | Marsden ...................... 428/429 |
| 4,665,066 A * | 5/1987 | Morin, Jr. ............. C07D 463/22 | 54/206 |
| 5,765,866 A * | 6/1998 | Canterberry ........ B60R 21/2644 | 280/741 |
| 6,293,983 B1 * | 9/2001 | More ............................. 55/486 |
| 6,311,527 B1 | 11/2001 | Monteiro et al. |
| 6,381,790 B2 | 5/2002 | Monteiro et al. |
| 6,423,408 B2 | 7/2002 | Okamoto |
| 6,497,123 B2 | 12/2002 | Monteiro et al. |
| 6,854,300 B2 | 2/2005 | Monteiro et al. |
| 7,197,901 B2 | 4/2007 | Monteiro et al. |
| 7,494,587 B2 * | 2/2009 | Yan et al. ...................... 210/222 |

(Continued)

FOREIGN PATENT DOCUMENTS

| CA | 2332024 A1 | 11/1999 |
|---|---|---|
| CN | 2156860 Y | 2/1994 |

(Continued)

OTHER PUBLICATIONS

Translation of JP 2007090286 to Oku et al.*

(Continued)

*Primary Examiner* — Mohammad M Ali
(74) *Attorney, Agent, or Firm* — Fish & Richardson P.C.

(57) ABSTRACT

The present disclosure provides an air cleaning filter that includes a ginseng extract, a binder and a supporting material, and a method of manufacturing the same. The present disclosure may remove or sterilize microbes, such as bacteria, viruses, fungi, and the like, and provide an air cleaning function along with antibiotic and deodorization functions as well as provide an air cleaning filter which is safe to the human body.

23 Claims, 5 Drawing Sheets

(56) References Cited

U.S. PATENT DOCUMENTS

| | | | |
|---|---|---|---|
| 7,754,252 B2 | 7/2010 | Kim | |
| 2001/0008690 A1 | 7/2001 | Okamoto | |
| 2001/0023513 A1 | 9/2001 | Monteiro et al. | |
| 2002/0013968 A1 | 2/2002 | Monteiro et al. | |
| 2002/0029594 A1 | 3/2002 | Monteiro et al. | |
| 2003/0047079 A1* | 3/2003 | Kaiser | 96/224 |
| 2005/0005653 A1 | 1/2005 | Monteiro et al. | |
| 2005/0279211 A1* | 12/2005 | Swofford | 96/226 |
| 2006/0127379 A1* | 6/2006 | Kim et al. | 424/93.45 |
| 2007/0209978 A1* | 9/2007 | Mitchell | 210/94 |
| 2008/0050398 A1* | 2/2008 | Bockmuehl et al. | 424/190.1 |
| 2008/0307807 A1* | 12/2008 | Graff et al. | 62/186 |
| 2009/0010801 A1* | 1/2009 | Murphy et al. | 422/4 |
| 2009/0011053 A1* | 1/2009 | Cho et al. | 424/728 |
| 2009/0052161 A1* | 2/2009 | Lee | 362/94 |
| 2010/0015283 A1* | 1/2010 | Jung et al. | 426/49 |
| 2011/0236452 A1* | 9/2011 | Yamamura et al. | 424/405 |
| 2011/0237492 A1* | 9/2011 | Bar-Or | A61K 38/07 514/1.1 |
| 2011/0293701 A1* | 12/2011 | Bratzler et al. | 424/450 |
| 2012/0000918 A1* | 1/2012 | Deane | B65D 81/3802 220/592.2 |
| 2012/0237406 A1 | 9/2012 | Lee | |

FOREIGN PATENT DOCUMENTS

| | | |
|---|---|---|
| CN | 1297784 A | 6/2001 |
| CN | 1738905 A | 2/2006 |
| CN | 101839534 A | 9/2010 |
| EP | 0688894 A1 | 12/1995 |
| JP | 3-111089 A | 5/1991 |
| JP | 2006-230956 A | 9/2006 |
| JP | 2007-090286 A | 4/2007 |
| KR | 10-2002-0037814 A | 5/2002 |
| KR | 10-2002-0043934 A | 6/2002 |
| KR | 10-2006-0071146 A | 6/2006 |
| WO | WO 99/58753 A1 | 11/1999 |
| WO | WO 2008/143372 A1 | 11/2008 |
| WO | WO 2010/008181 A2 | 1/2010 |
| WO | WO 2011/055893 A1 | 5/2011 |

OTHER PUBLICATIONS

Chinese Office Action dated Jul. 2, 2014 for Chinese Application No. 2013100455958, with English Translation, 15 pages.
Korean Notice of Allowance for Application No. 10-2011-0108952, dated Jan. 17, 2013 with English Translation, 5 pages.
PCT International Search Report and Written Opinion for Application No. PCT/KR2012/008777, dated Feb. 19, 2013, 12 pages.
PCT International Search Report and Written Opinion for Application No. PCT/KR2012/008775, dated Feb. 19, 2013, 9 pages.
Chinese Office Action dated May 11, 2015 for Chinese Application No. 201310045595.8, with English Translation, 15 Pages.
European Search Report dated May 2, 2013 for Application No. 13153987, 6 pages.
Lu Han et al., "Ginsenoside Rb1 in Asymmetric Somatic Hybrid Calli of Daucus carota with Panax quinquefolius", Plant Cell Reports, Springer, Berlin, DE, vol. 28, No. 4, Feb. 8, 2009, pp. 627-638, XP019709145.

* cited by examiner

AIR CLEANING FILTER AND METHOD FOR MANUFACTURING THE SAME

CROSS-REFERENCE TO RELATED APPLICATIONS

This application claims the benefit of Korean Patent Application No. 10-2012-0012005, filed on Feb. 6, 2012, which is hereby incorporated by reference for all purposes as if fully set forth herein.

FIELD

The present disclosure relates to an air cleaning filter and a method for manufacturing the same.

BACKGROUND

In recent years, various air cleaning devices for removing foreign substances or microbes have been developed. An air cleaning filter may be used for the air cleaning device, and filters having various forms and characteristics may be required based on the type of objects being removed, the size of the objects, features of the objects, or the like. Various filters have been developed based on these characteristics.

Some filters have antibiotic or sterile properties and can remove or sterilize microbes, such as bacteria, viruses, fungi, and the like, thereby achieving satisfying air cleaning effect. The antibiotic and sterile properties may be useful in an environment where air circulation is required and microbes are easily propagated in a sealed space for a long period of time.

In particular, such air cleaning, sterilization and deodorization functions may be useful in a household appliance, such as a refrigerator storing easily spoiled foods for a long period of time. Moreover, a household appliance may have a restriction that safe materials, which are non-hazardous to human body, be used. Accordingly, typical antibiotic substances or microbicides may not be appropriate.

SUMMARY

In one aspect, an air cleaning filter includes a ginseng extract, a supporting material configured to filter air flowing through the air cleaning filter, and a binder configured to bind the ginseng extract to the supporting material.

Implementations may include one or more of the following features. For example, the air cleaning filter may include an antibiotic substance having sterilization and antibiotic functions. In this example, the antibiotic substance may include at least one of phthalaldehyde (PA), potassium disulphite (PD), bronopol, sodium desoxycholate, glutaraldehyde, sodium desoxycholate, and quaternary ammonium.

In addition, the binder may include at least one of polyvinylpyrrolidone iodine (PVPI) and norspermidine (NS, bis(3-aminopropyl)octylamine. The binder also may include at least one of silicone-modified acrylic resin, silicone-modified urethane resin, silicone-modified epoxy resin, silicone-modified vinyl resin, urethane resin, acrylic resin, vinyl resin, and silicone resin.

In some implementations, the ginseng extract may include at least one of a ginseng leaf extract, a fermented ginseng rootlet extract, and a fermented ginseng main root extract. The ginseng extract also may include at least one of an extract solution of ginseng, a concentrated extract solution of ginseng, and a dried extract solution of ginseng.

In some examples, the supporting material may include at least one of a non-woven fabric, a paper fiber, a glass fiber, an ion-exchange fiber, a cellulose fiber, an asbestos fiber, activated carbon, titanium dioxide, zinc, copper, and aluminium. The air cleaning filter further may include a metal.

The supporting material may be impregnated or coated with an antibiotic composite that includes the ginseng extract, the antibiotic substance, and the binder. A weight ratio of a sum of the ginseng extract and the antibiotic substance, and the antibiotic binder may be 1:2 to 1:80.

In another aspect, a filter module includes a housing that defines an air suction port and an air discharge port, an air cleaning filter unit disposed within the housing and having a filter, and a blower fan. The air cleaning filter unit includes a ginseng extract and a binder that binds the ginseng extract to the filter.

Implementations may include one or more of the following features. For example, the air cleaning filter unit may include a first filter, a second filter, and a third filter. A mesh size of the first filter, the second filter, and the third filter sequentially disposed from the air suction port toward the air discharge port may decrease from the first filter to the third filter.

In addition, the air cleaning filter unit may include an antibiotic substance, a metal, and a coating layer that is coated on the filter and that includes the ginseng extract and the binder. The air cleaning filter unit or the filter may be coupled to the housing in an integrated or detachable structure.

In some implementations, a refrigerator may include a main body provided with a storage space for refrigerated storage, a compressor provided within the main body to compress refrigerant, and one or more doors configured to selectively open or close the storage space. In these implementations, the refrigerator may include the filter module mounted within the storage space. Further, in these implementations, the main body may include an inner case defining the storage space, an outer case defining an external appearance of the refrigerator, a cool air duct positioned in a space between the inner case and the outer case and configured to supply cool air, and a multi duct positioned in a space between the inner case and the outer case and having one or more discharge ports that receive sterile air discharged from the filter module and deliver the received sterile air to the storage space. The refrigerator may include a controller configured to control operation of the filter module.

In yet another aspect, a method of manufacturing an air cleaning filter includes producing a ginseng extract by preparing crushed ginseng material by crushing at least one of ginseng rootlets, ginseng leaves, and ginseng main roots, sterilizing a mixture produced by mixing the crushed ginseng material with a solvent, and preparing a raw ginseng extract solution by mixing the mixture with alcohol. The method also includes preparing an antibiotic composite solution by mixing a composite comprising the ginseng extract, an antibiotic binder, and a solvent. The method further includes fixing the antibiotic composite solution to a supporting material or a filter.

Implementations may include one or more of the following features. For example, after sterilizing the mixture and prior to preparing the raw ginseng extract solution, the method may include preparing a sterile crushed ginseng material by cooling the sterilized mixture, preparing a ginseng culture fluid by adding a culture fluid to the sterile crushed ginseng material, and preparing a fermented mixture by fermenting the ginseng culture fluid. In this example, preparing the fermented mixture by fermenting the ginseng culture fluid may be carried out at temperatures of 25 to 35° C. for 0.5 to 3 days. Also, the culture fluid may include at least one of *lactobacillus plantarum* (*L. plantarum*), *candida utilis* (*C. utilis*), and *aspergillus oryza* (*A. oryzae*).

In some implementations, the method may include concentrating and pulverizing the raw ginseng extract solution to produce a ginseng extract power. The antibiotic composite solution may include the ginseng extract powder in a weight ratio of 0.001 to 30 weight percentage. The antibiotic composite solution may include a metal.

DETAILED DESCRIPTION

Figure 1:
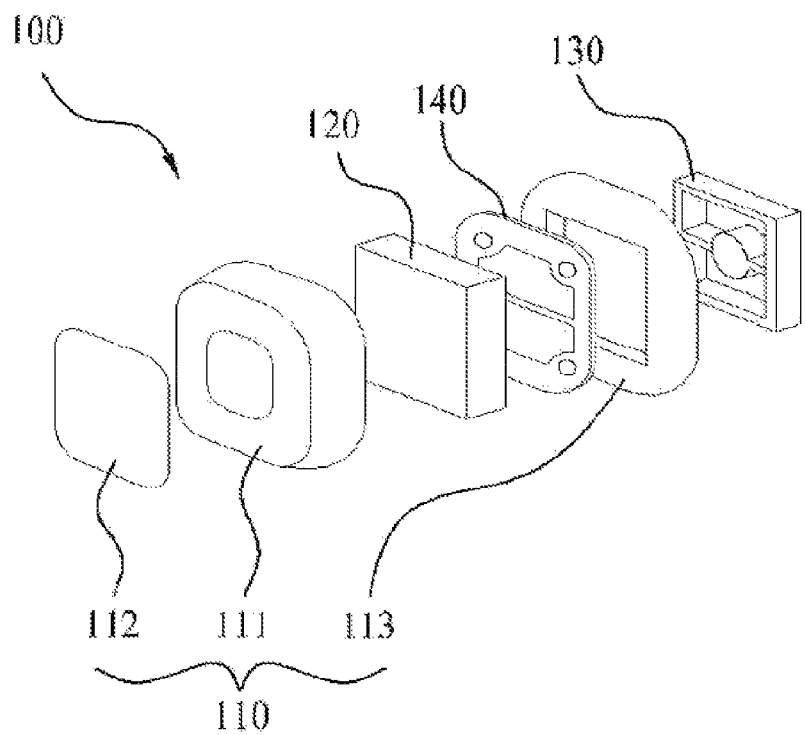
FIG. 1 is an exploded oblique view illustrating an example filter module.

An air cleaning filter of the present disclosure may include a ginseng extract, a binder and a supporting material. The ginseng extract may be an extract of ginseng, including a processed ginseng extract, such as red ginseng, black ginseng, and the like as well as an unprocessed ginseng extract. The ginseng extract may be any one of a ginseng rootlet extract extracted from ginseng rootlets, a ginseng leaf extract extracted from ginseng leaves, a ginseng main root extract extracted from ginseng main roots, a fermented ginseng rootlet extract extracted from fermented ginseng rootlets, a fermented ginseng leaf extract extracted from fermented ginseng leaves, a fermented ginseng main root extract extracted from fermented ginseng main roots, and any combination of the above-referenced ginseng extracts.

The ginseng extract is safe to humans and may assist in removing and/or sterilizing microbes. Specifically, the ginseng extract may be effective in removing general bacteria, removing pathogenic bacteria, such as food poisoning bacteria, removing viruses which cause contagious diseases, such as bird flu or swine flu in recent years, and/or removing fungi, which are difficult to remove because they are propagated from spores like filamentous fungi.

Moreover, the ginseng extract may be a substance extracted from ginseng that is used for drugs or food additives and, thus, non-hazardous to the human body, and usable in a space directly in contact with the human body and/or directly in contact with foods.

In some implementations, the ginseng extract is produced using ginseng by-products of any combination of one or more of ginseng rootlets and ginseng leaves. In these implementations, the ginseng extract may be produced using ginseng bi-products unusable for drugs of ginseng or disposed of after making drugs of ginseng. Using unusable or disposed of bi-products may enhance economic efficiency as well as achieve benefits in the environmental aspect.

In particular, when the ginseng extract is composed of a fermented ginseng extract fermented and extracted from any crushed ginseng material selected from ginseng rootlets, ginseng leaves, ginseng main roots and their combinations, the antibiotic and sterilization effect of the ginseng extract may be increased by the fermentation process.

Moreover, when the ginseng extract is composed of the ginseng leaf extract, fermented ginseng rootlet extract, and fermented ginseng main root extract, the ginseng extract may have enhanced antibiotic and sterilization effects as compared to other extracts. The ginseng leaf extract and fermented ginseng rootlet extract may achieve an excellent effect in the economic and/or environmental aspect along with an excellent antibiotic effect.

In some examples, the ginseng extract may include any combination of one or more of an extract solution of ginseng, a concentrated extract solution of ginseng, and a dried extract solution of ginseng. When the dried extract solution of ginseng is used for the ginseng extract, it may be possible to maintain the antibiotic and sterilization performance as well as facilitate the storage and transfer. The dried extract solution of ginseng may be a powder of dried ginseng extract or frozen and dried ginseng extract.

The binder may fix the ginseng extract to a supporting material capable of impregnating the ginseng extract or a filter having an effect of removing foreign substances, such as dust through typical air filtration along with the role of the supporting material, and attach the ginseng extract to the supporting material or filter in spite of the air pressure load of the supporting material or filter.

For the binder, any binder capable of attaching the ginseng extract to the supporting material or filter may be applicable, and it may not be particularly limited.

For the binder, antibiotic binders having an antibiotic function along with an adhesive force, such as polyvinylpyrrolidone iodine (PVPI), norspermidine (NS, bis(3-aminopropyl) octylamine), and their combinations may be applicable.

Organic or inorganic hybrid binders, such as silicone-modified acrylic resin, silicone-modified urethane resin, silicone-modified epoxy resin, silicone-modified vinyl resin, urethane resin, acrylic resin, vinyl resin, silicone resin and their combinations may be applicable. Epoxy resin may be used for the binder.

In some implementations, a silane compound, such as organic silane or alkoxysilane, which is used for the silicon modification of the binder among the organic or inorganic hybrid binders, may be any one of methyltrichlorosilane, vinyltrichlorosilane, 3-glycidoxypropyltrimethoxysilane, tetra-ethyl orthosilicate, 3-aminopropyltrimethoxysilane, 3-methacryloxypropyltri-methoxysilane, and vinyltrimethoxysilane.

For the silicone-modified organic or inorganic hybrid binders, the silane compound and the binder resin may be produced using hydrolysis under a solvent, such as water or alcohol, and inorganic acids, such as hydrochloric acid, sulphuric acid, and nitric acid, may be used for the hydrolysis catalyst.

For the binder, the antibiotic binders and the organic or inorganic hybrid binders may be applicable in a mixed manner. In this case, the binder itself can sufficiently fix the ginseng extract to the supporting material or filter while having the antibiotic and sterilization performance, thus enhancing the antibiotic and sterilization performance of the air cleaning filter.

In particular, when polyvinylpyrrolidone iodine (PVPI) is applied to the binder, it may be possible to obtain a sufficient adhesive effect even with a small amount, and at the same time, exhibit an excellent sterilization characteristic, thereby enhancing the antibiotic and sterilization performance of the air cleaning filter.

For the supporting material, any one capable of fixing the ginseng extract with impregnation or coating may be applicable without any limitation, and any one that can be contained in the air cleaning filter or provided with a function as an air cleaning filter itself may be applicable without any limitation in the type, shape, size and production method.

The supporting material may be composed of a material such as a textile, a metal, a plastic or the like, and may include any one of a non-woven fabric, a paper fiber, a glass fiber, an ion-exchange fiber, a cellulose fiber, an asbestos fiber, activated carbon, titanium dioxide, zinc, copper, and aluminium and their combinations.

The supporting material may be produced in various shapes including a honeycomb shape, a particle shape, a net shape, a filter paper shape, a cotton shape, a mesh type, a plate shape and a groove shape. The various shapes they may be modified in a suitable manner or mixed and used for the supporting material.

Furthermore, the supporting material may be or include a filter, such as a deodorizing filter which is used for various household appliances including a refrigerator, air conditioner, and the like, a HEPA filter, and a filter of the air cleaning device in a vehicle, and the like.

The non-woven fabric may be a dried non-woven fabric or wet non-woven fabric, and the dried non-woven fabric may be polypropylene (PP), polyethylene terephthalate (PET), polyethylene (PE), polyamide, nylon, and their combinations, and may be in the form of a metal sol.

Furthermore, the supporting material may be an air filter. For the air filter, any filter that filters air may be applicable, and specifically, a non-woven fabric including polypropylene may be used, or the air filter may be a zebra filter.

In particular, when an air filter having an effect of removing foreign substances, such as dust, through typical air filtration along with the role of the supporting material is applied to an air cleaning filter, antibiotic and sterile characteristics along with a typical air cleaning function may be provided to the air cleaning filter at the same time, thereby enhancing the performance of the air cleaning filter.

The air cleaning filter may further include an antibiotic substance, and any material known for its sterile, antibiotic and anti-bacterial effect may be used for the antibiotic substance.

In some implementations, the antibiotic substance may include any one of phthalaldehyde (PA), potassium disulphite (PD), bronopol, sodium desoxycholate, glutaraldehyde, sodium desoxycholate, quaternary ammonium and their combinations. When they are applied to the antibiotic substance, their safety has been verified to an extent that they can be used for foods, and thus may be non-hazardous to the human body while enhancing the antibiotic and sterilization effect of the air cleaning filter. In particular, glutaraldehyde may connect proteins with each other to inhibit the activity of microbes with enzyme immobilization, and the sodium desoxycholate may have an effect on cell membranes to inhibit cell growth, and the quaternary ammonium may increase the pH to aggravate the survival condition of microbes.

The air cleaning filter may further include a metal, and in this case, the antibiotic and sterilization performance of the air cleaning filter may be enhanced. The metal may include any one of Ag, Cu, Zn, Ca, Mn and their combinations, or may be in the form of a metal sol.

An antibiotic composite having the ginseng extract, the antibiotic substance and the binder is impregnated in or coated on the supporting material for the air cleaning filter. The impregnation or coating may be carried out using known techniques, and a dipping method, a roll method, a spray method, and the like may be used, but other methods also may be possible. When the antibiotic composite is coated on the supporting material, the coating layer may have a thickness of several nanometers to tens of several micrometers. Furthermore, the antibiotic composite may further include a metal.

For the antibiotic composite, content capable of maintaining an antibiotic function and adhesive capability (in which the antibiotic composite is coated on the supporting material to maintain an antibiotic function) may be applicable, and specifically, the weight ratio of (ginseng extract+antibiotic substance):(antibiotic binder) may be 1:2 to 1:80, 1:5 to 1:40, or 1:7.5 to 1:10. When the antibiotic composite is applied with the content ratio, it may be possible to optimize antibiotic and adhesive capabilities required for the air cleaning filter and enhance economic efficiency.

The metal may be provided in a volume ratio of 1 to 10 times on the basis of the content of the ginseng extract, and the antibiotic substance may be provided in a weight ratio of 0.01 to 10 on the basis of the ginseng extract.

The air cleaning filter includes a ginseng extract and, thus, is non-hazardous to the human body and also has an antibiotic and sterilization effect, and may be effective in removing general bacteria as well as removing pathogenic bacteria such as food poisoning bacteria, viruses, and fungi. As a result, it may be possible to obtain an excellent effect of removing microbes in the air along with the air cleaning function, thus providing a deodorizing effect. According to the present disclosure, the term sterilization of antibiosis may be used to refer to the removal of fungi, the removal of viruses, as well as the removal of bacteria, unless particularly specified otherwise.

Figure 2:
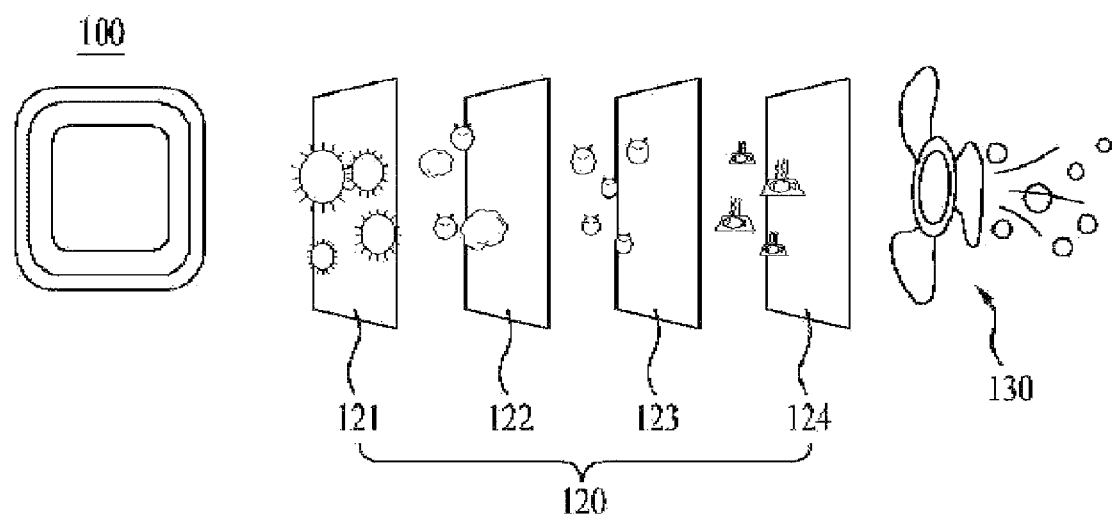
FIG. 2 is a conceptual view that illustrates an example operation state of the example filter module illustrated in FIG. 1.

A filter module may include a ginseng extract and a binder in the air cleaning filter unit. Referring to FIGS. 1 and 2, an example filter module 100 is described below.

The filter module 100 may include a housing 110 having an air suction port and an air discharge port, an air cleaning filter unit 120 disposed within the housing 110, and a blower fan 130 configured to inhale air to the filter module 100 and discharge the sterilized air to the outside.

Furthermore, the casing 110 may have various shapes and structures, and, referring to FIG. 1, the casing 110 may include a front housing 111 provided with an air suction port, and a rear housing 113 coupled to a rear side of the front housing 111 to have an air discharge port for the mounting of the blower fan 130, and a front panel 112 mounted at a front side of the front housing 111.

In such a structure, air is inhaled through a gap between the front panel 112 and the front housing 111, and the inhaled air is passed through the air suction port of the front housing 111 to reach the air cleaning filter unit 120.

The air cleaning filter unit 120 may be formed within the housing 110 as an integral body or detachably accommodated as a replaceable structure.

Furthermore, a slit plate 140 for guiding the flow of air between the air cleaning filter unit 120 and blower fan 130 may be disposed at the filter module 100.

The air cleaning filter unit 120 may include a plurality of filters sequentially disposed along the air suction port side of the casing 110 toward the air discharge port side thereof, and the plurality of filters may be divided into a first filter 121, a second filter 122, and a third filter 123 to perform the antibiotic and sterilization treatment of the air through a plurality of steps.

Here, the size of a mesh (pores of the filter) may be decreased from the first filter 121 to the third filter 123. For example, the first filter 121 may have a mesh of greater than about 100 μm, and the second filter 122 may have a mesh of greater than about 5 μm, and the third filter 123 may have a mesh of greater than about 2.5 μm.

Furthermore, the filter module 100 may further include a deodorizing filter 124 for deodorizing the air that passes through the filters 121, 122, 123 included in the air cleaning filter unit.

The filter module 100 having the foregoing structure may maintain air clean through three-step sterilization and one-step deodorization processes.

Furthermore, a filter included in the air cleaning filter unit may include a ginseng extract and a binder, and a coating layer having any one of the ginseng extract, antibiotic substance, binder, metal and their combinations may be formed on the filter.

The description of the ginseng extract, antibiotic substance, binder, metal and their content has been provided above, and, thus, is being referenced, rather than repeated.

The ginseng extract and a coating layer including the same may exhibit an effect on the removal of microbes, such as bacteria, viruses, and fungi, thereby providing antibiotic and sterilization performance to the filter module and securing stability.

Furthermore, the filters 121 to 124 included in the air cleaning filter unit 120 may have a zebra pattern having a triangular shaped curvature structure to increase the area of the coating layer.

In some examples, the filter module 100 may further include an anti-allergen filter, and the anti-allergen filter may include any one of activated carbon, silver (Au), allercatcher fiber, Co-phthalocyanine, and Fe-phthalocyanine, and the activated carbon may be an impregnated activated carbon including T-TS impregnated with silver, T-E for selectively absorbing ethylene or T-TS for selectively absorbing aldehyde mostly generated from bean paste and fermented foods.

Figure 3:
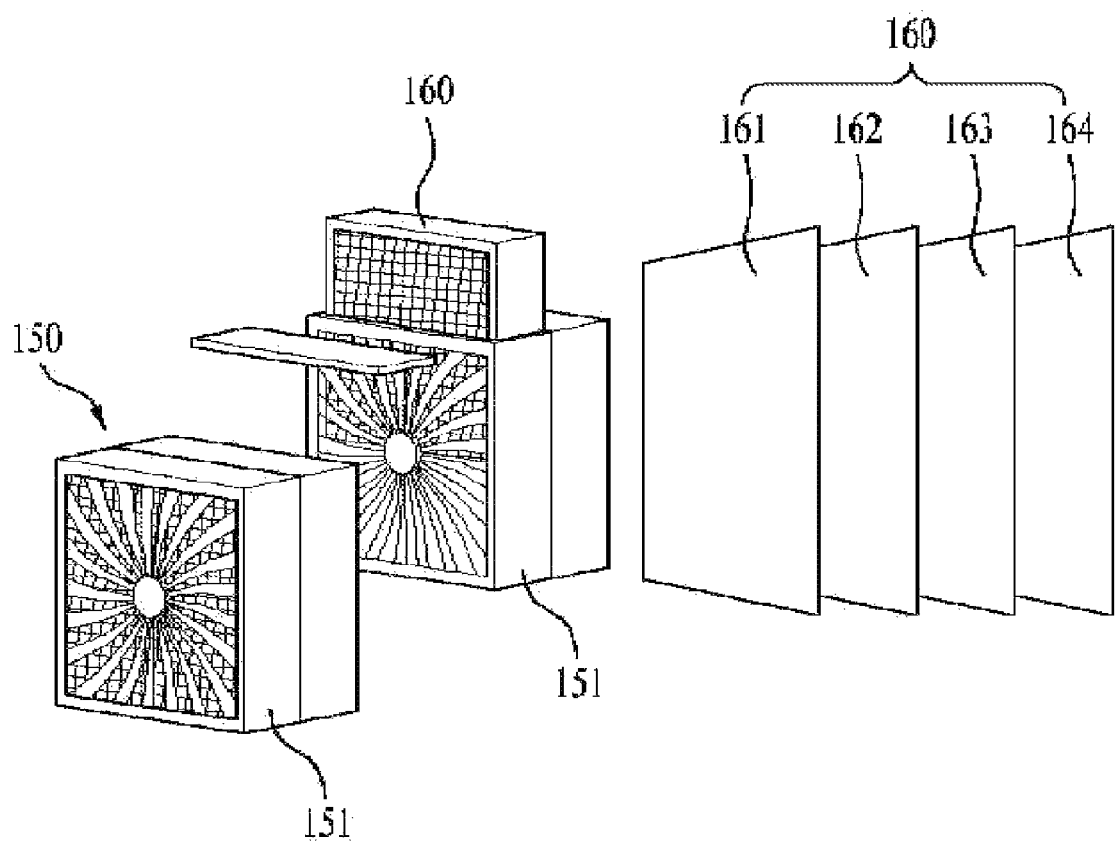
FIG. 3 is a perspective view illustrating another example filter module.

Referring to FIG. 3, an example filter module 150 may include a housing 151 having an air suction port and an air discharge port, a filter box 160 detachably accommodated in the housing 151, and a blower fan disposed within the housing. The filter module 150 illustrated in FIG. 3 is different from the filter module 100 only in that the filter module 150 is incorporated in the housing and a filter box is separately provided therein. Therefore, the above description of similar portions to the filter module 100 is referenced, rather than repeated.

The filter box 160 may include a plurality of filters 161, 162, 163 included in the foregoing plurality of air cleaning filter units, a deodorizing filter 164, and their combinations. The filter module 150 may be provided with a filter box 160 separately from the housing 151 in an integral body, thereby facilitating the replacement of the air cleaning filter unit.

Figure 4:
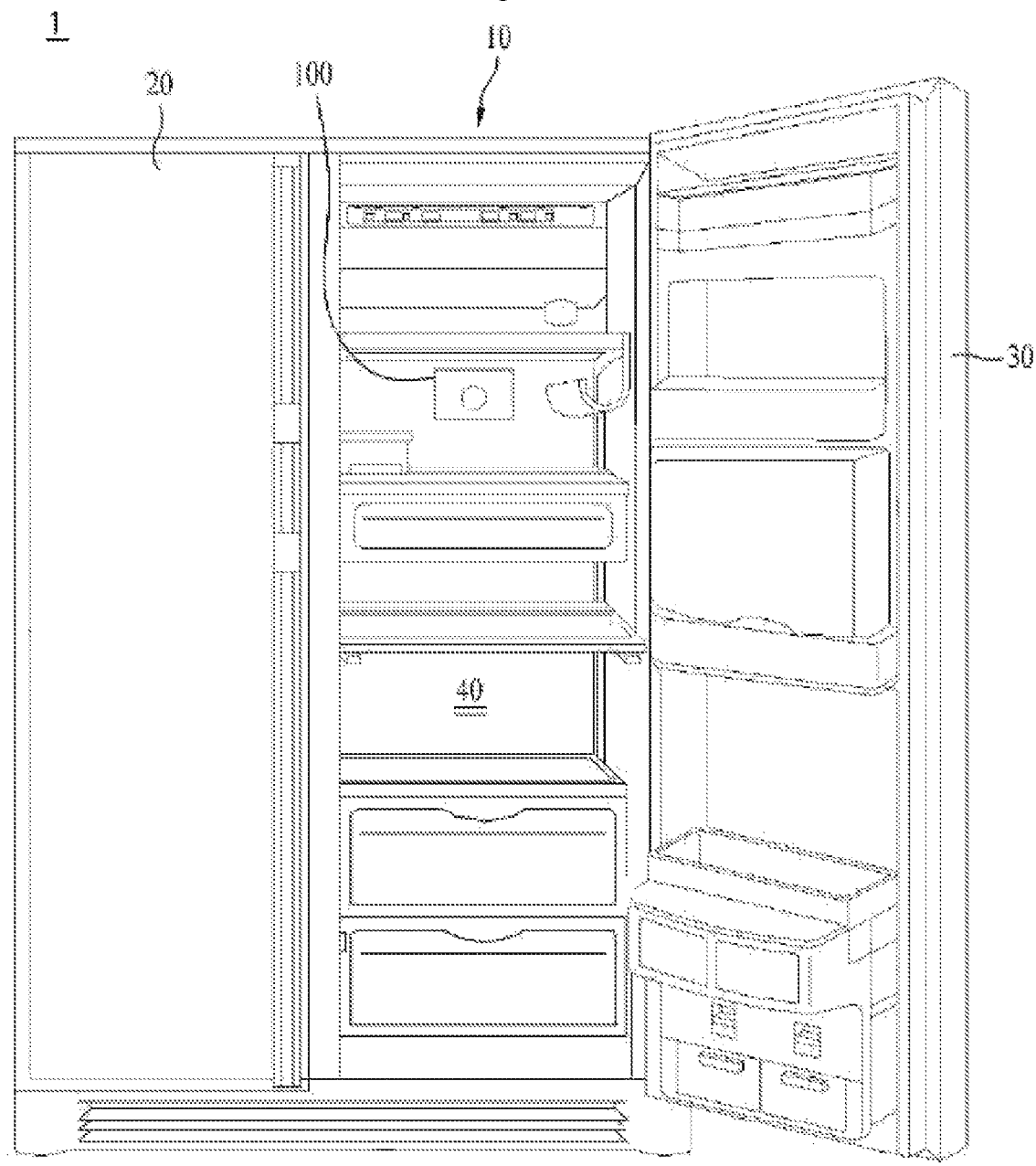
FIG. 4 is a front view illustrating an inner portion of an example refrigerator to which an example filter module is applied.
Figure 5:
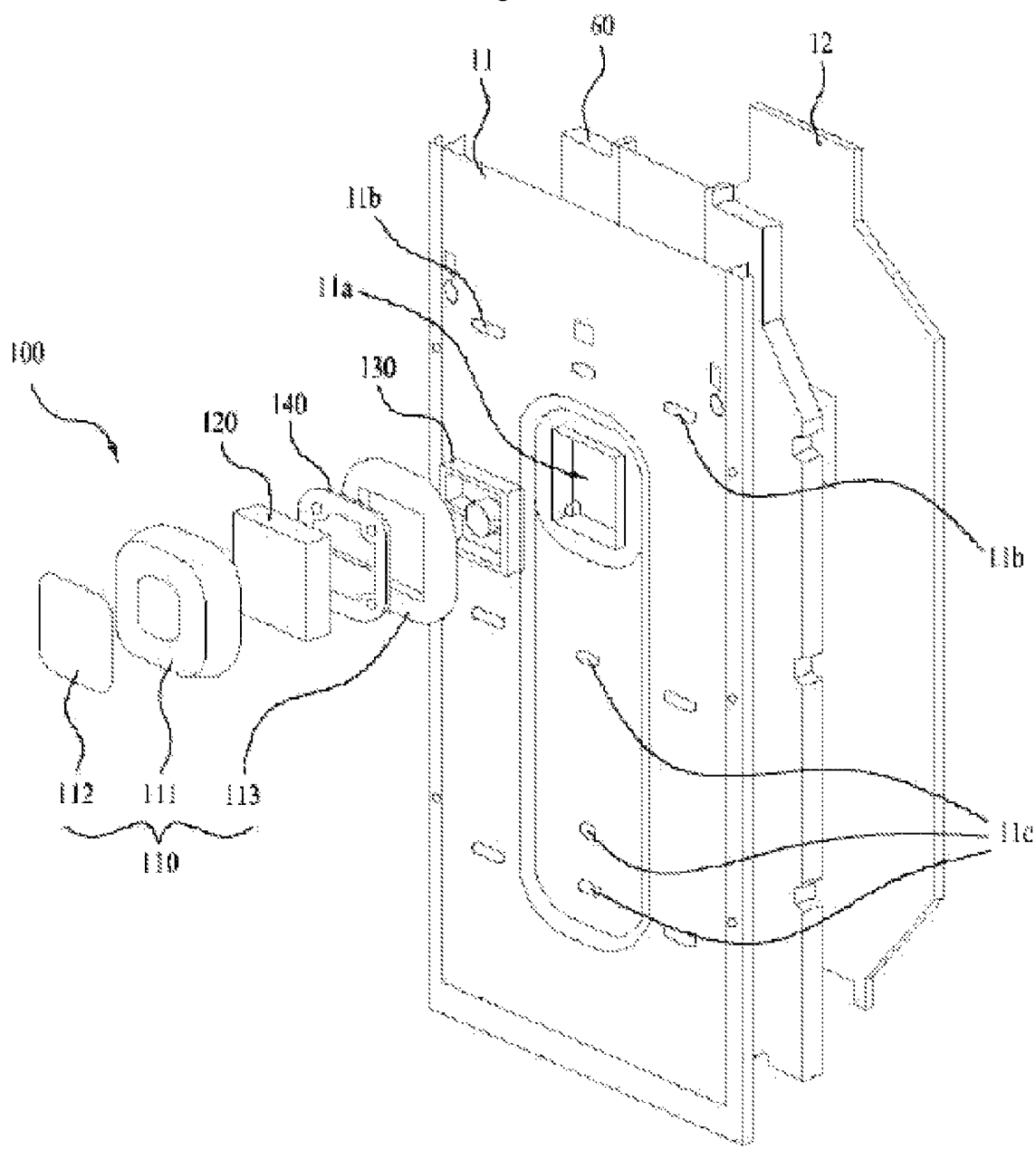
FIG. 5 is an exploded oblique view illustrating an example structure in which an example filter module is mounted in the example refrigerator illustrated in FIG. 4.
Figure 6:
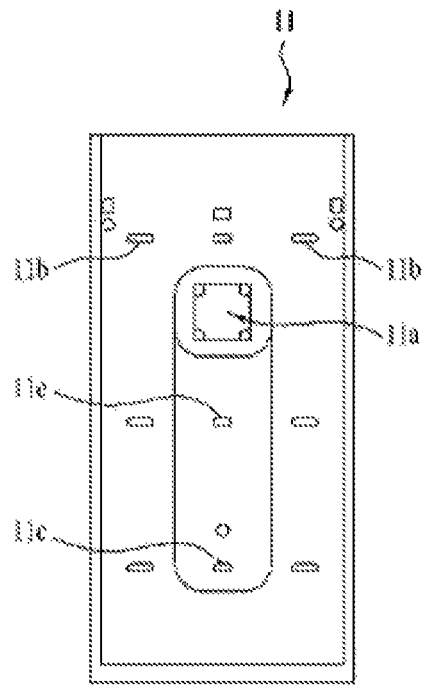
FIG. 6 is a front view illustrating the inside of the example refrigerator illustrated in FIG. 4.

The filter module may be used for air cleaning and deodorizing a refrigerator for storing foods. FIGS. 4 through 6 illustrate an example in which the filter module is applied to a refrigerator, and referring to FIGS. 4 through 6, the refrigerator 1 may include a main body 10 provided with one or more storage spaces 40 for low temperature storage, a compressor provided within the main body 10 to compress refrigerant, one or more doors 20, 30 rotatably mounted on the main body 10 to selectively open or close the storage space 40, a filter module 100 mounted within the storage space of the main body 10, and a controller configured to control the operation of the filter module 100.

The description of the filter module 100, a filter including the same, a coating layer formed on the filter, and a ginseng extract, an antibiotic substance, a binder, a metal and their content was provided above and, thus, is referenced, rather than repeated.

The refrigerator 1 may include a main body 10 providing a space and external appearance capable of storing foods and food containers, and the main body 10 may be formed in a substantially rectangular shape, and also formed in a state that the front surface is open to accommodate foods and food containers.

The main body 10 of the refrigerator 1 may include an outer case 12 forming an external appearance thereof, and one or more inner cases 11 disposed within the outer case 12 to provide a storage space for refrigerating or freezing foods.

Referring to FIG. 5, a cool air duct 60 for supplying cool air to an inner portion of the storage space 40 is disposed between the inner case 11 and outer case 12.

The doors 20, 30 are rotatably mounted at an open front surface of the main body 10 to selectively open or close the open front surface of the storage space of the main body 10. In FIG. 4, a so-called side-by-side refrigerator in which the cooling chamber and refrigerating chamber are disposed side by side is illustrated, but the described techniques and structures are not limited to this configuration.

In addition, in recent years, various functions have been added for the convenience of using the refrigerator 1, and in order to implement such functions, the doors 20, 30 may further include a dispenser capable of taking out purified water or ice directly from an external space, a home bar capable of conveniently accommodating or storing foods or food containers at a predetermined level, and the like.

The main body 10 is provided with a cool air duct 60 for supplying cool air to the storage space 40 and a multi duct 70 (see FIG. 7) having one or more discharge ports 71 for inhaling sterile air discharged from the filter module 100 and delivering the inhaled sterile air to the storage space 40, respectively, in a space between the inner case 11 and the outer case 12.

An opening portion 11a for mounting the filter module 100, a cool air supply hole 11b for supplying cool air to an inner portion of the storage space, and a flow hole 11c for supplying sterile air to an inner portion of the storage space through the multi duct 70 may be provided in the inner case 11.

Furthermore, the flow holes 11c may be provided at locations corresponding to the discharge ports 71 of the multi duct 70, respectively, and sterile air may be inhaled to an inner portion of the inner case 11 through the flow holes 11c.

Specifically, air inhaled to the filter module 100 through the air suction port of the casing 110 from the storage space is sterilized and deodorized during the process of passing through the air cleaning filter unit 120 included in the sterile filter, and sterile air is inhaled to an inner portion of the multi duct 70 along the opening portion 11a of the inner case through the air discharge port of the casing 110.

Then, sterile air flowing through an inner portion of the multi duct 70 is sequentially passed through the discharge port 71 of the multi duct 70 and the flow hole 11c of the inner case 11 and supplied to the storage space.

In some examples, the cool air duct 60 may be formed in a shape of surrounding the multi duct 70 to increase space usability between the inner case 11 and outer case 12.

Figure 7:
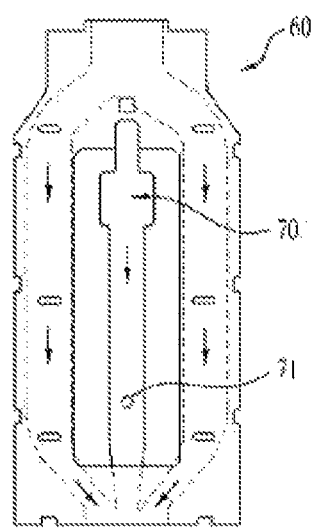
FIG. 7 is a front view illustrating flow of cool air in the example refrigerator illustrated in FIG. 4.

Furthermore, referring to FIG. 7, an end portion of the multi duct 70 may be connected to the cool air duct 60 to inhale sterile air and cool air together to an inner portion of the inner case 11, but also separated from the cool air duct 60 to separately inhale sterile air and cool air to an inner portion of the inner case 11.

In some implementations, the refrigerator may include a controller capable of controlling the operation of the filter module 100, and the controller may be a central controller for controlling the entire operation of the refrigerator or may be a local controller for controlling only the operation of the filter module 100.

The controller may further include a display unit for displaying the state of the storage space, the operation state of the filter module 100, or the replacement period of the filter module 100 for the user.

The operation mode of the filter module 100 may include a manual mode in which the user directly enters ON/OFF in a selective manner as required and an auto mode in which the filter module 100 is automatically operated based on a predetermined operating condition.

The auto mode may determine an operating condition by considering an accumulated time of the compressor, an opening frequency and/or opening time of the door, and the like.

The controller turns on the filter module during a first time and turns off the filter module during a second time, and the on and off of the filter module may be repeated at a predetermined frequency. For example, the accumulated time of the compressor is about 5 hours, and the first time is about 10 minutes and the second time is about 5 minutes.

In addition, the controller may turn on the filter module 100 for a predetermined period of time based on the switching of the door 20, namely, when the door 20 is open or closed, and the controller may turn on the filter module 100 for a predetermined period of time when the door is closed according to at least one of the opening frequency of the door 20 and the opening time of the door. In this regard, when the door 20 is opened and closed, the accommodation of foods may be most likely carried out, and external air is inhaled to an inner portion of the storage space, thereby performing sterilization through the filter module 100.

Considering the user's behavior, the frequency and time of opening the door may be increased during the morning/lunch/evening time zones, and the operating condition of the filter module 100 may be determined based on the actual usage cycle.

The operating period of the compressor may be determined based on the foregoing actual usage cycle, and thus the compressor may be operated for an accumulated 5 hours and then turned off for 3 hours based on the 8-hour period three times each day.

In some implementations, when a lot of foods are accommodated in the storage space or more powerful sterilization is required, the filter module 100 may be operated in a power mode. For instance, the filter module 100 may be operated for 4 hours (16 times) by repeating it on and off for 10 and 5 minutes, respectively, (per once).

The controller may turn off the operation of the filter module when the door is open during the operation of the filter module 100, and turn on the filter module 100 for the remaining time and frequency after closing the door.

Furthermore, the controller may turn off the operation of the filter module when a defrosting operation is started during the operation of the filter module 100, and turn on the filter module 100 for the remaining period of time and remaining number of times after the defrosting operation is terminated.

The refrigerator may include a filter module including an air cleaning filter to maintain air in a sterilized state within the storage space and, due to this, freshness of foods or the like stored in the refrigerator may be maintained for a longer period of time. The air cleaning filter included in the filter module may include ingredients extracted from ginseng that has been used for drugs for a long period of time, which are effective in removing microbes containing bacteria, viruses, fungi, and the like as well as being non-hazardous to the human body.

A method of manufacturing an air cleaning filter may include an extract production step, a solution production step, and a fixation step.

The extract production step is a process of producing a ginseng extract, and the solution production step is a process of mixing a composite containing the ginseng extract, an antibiotic substance, an antibiotic binder and a solvent to produce an antibiotic composite solution, and the fixation step is a process of fixing the antibiotic composite solution to a supporting material.

For the solvent, any solvent capable of dissolving the ginseng extract, antibiotic substance, and binder may be used without any particular limitation, and specifically, water and ethanol may be applied as the solvent.

The description of the ginseng extract, the antibiotic substance, the antibiotic binder, their content, the supporting material and the air cleaning filter has been provided above and, thus, is referenced, rather than repeated.

The extract production step may include a crushing process for crushing any one of ginseng rootlets, ginseng leaves, ginseng main roots and their combinations to produce a crushed ginseng material, a sterilization process for sterilizing a mixture containing the crushed ginseng material and sterile solvent (for example, water), and an extraction process for mixing the mixture with alcohol to produce a ginseng extract.

For the crushing process, any process capable of crushing any one of ginseng rootlets, ginseng leaves, ginseng main roots and their combinations may be used, and a homogenizer may be used. The size of the crushed ginseng material may not be particularly limited, and any size capable of enhancing the efficiency of the sterilization and extraction processes may be applicable thereto.

For the sterilization process, any method capable of sterilizing the crushed ginseng material may be used, and a high pressure steam sterilization method may be applicable thereto. According to the high pressure steam sterilization method, the mixture may be treated at 1.2 atm and 121° C. for more than 15 minutes. The sterilization method may allow removal of unnecessary microbes contained in the crushed ginseng material, and facilitate the extraction of the ginseng extract from the crushed ginseng material.

The extraction process may include a process of mixing the crushed ginseng material with alcohol to produce a ginseng extract. Any alcohol that can be used for extraction may be used without any limitation, and the alcohol may be any one of methanol, ethanol, and their combinations. For the process of producing the ginseng extract, any process capable of extracting effective ingredients from the crushed ginseng material may be applicable without any limitation, and the process may be a process for mixing the crushed ginseng material with alcohol to agitate and extract the ginseng extract from the material.

The extract production step may further include a fermentation process between the sterilization process and the extraction process. The fermentation process may include a first fermentation process for cooling the sterilized mixture to produce a sterile crushed ginseng material, a second fermentation process for adding a culture fluid to the sterile crushed ginseng material to produce a ginseng culture fluid, and a third fermentation process for fermenting the ginseng culture fluid to produce a fermented and crushed ginseng material. Where the extract production step further includes the fermentation process, a high molecular weight ginsenoside ingredient may be low-molecularized to transform the ginsenoside ingredient in a unique way, thereby further enhancing sterilization function.

The third fermentation process may be carried out at temperatures of 25 to 35° C. for 0.5 to 3 days. When fermentation is carried out in the temperature and time range, each strain may be cultured under the optimal growth temperature and thus it may be advantageous in low-molecularizing the ingredients of ginseng.

The culture fluid may include any one of *lactobacillus plantarum* (*L. plantarum*), *candida utilis* (*C. utilis*), *aspergillus oryza* (*A. oryzae*) and their combinations. When the ginseng extract is produced using microbes contained in the culture fluid, it may be possible to enhance the efficiency of extracting the effective ingredients of the ginseng extract.

The culture fluid may contain 0.1 to 10 parts by weight of the sterile crushed ginseng material based on 100 parts by weight.

The extract production step may further include a pulverization process subsequent to the extraction process, and the pulverization process may be a process of concentrating and pulverizing the extracted ginseng extract to produce a ginseng extract power, and specifically, the ginseng extract may be concentrated and pulverized using a known drying process or a known freeze drying process.

The extract production step may be carried out at temperatures of 40 to 100° C., and carried out at temperatures of 50 to 75° C. The extract production step may repeatedly extract the crushed ginseng material three to four times to produce a ginseng extract.

The antibiotic composite solution may contain the ginseng extract powder in 0.001 to 20 weight % based on the entire antibiotic composite solution, and may contain the ginseng extract powder in 0.1 to 10 weight %, and may contain the ginseng extract powder in 0.3 to 5 weight %. When the content of the ginseng extract powder is less than 0.001, antibiotic performance due to the ginseng extract may be insignificant, and when greater than 30 weight %, the economic efficiency may be low. Furthermore, when the antibiotic composite solution contains the ginseng extract powder in the above content range, it may provide a sufficient antibiotic performance for an air cleaning filter coated with the same while being non-hazardous to the human body.

The antibiotic composite solution may contain the antibiotic substance in 0.0001 to 10 weight % based on the entire antibiotic composite solution, may contain the antibiotic composite solution in 0.01 to 5 weight %, and may contain the antibiotic composite solution in 0.08 to 3 weight %. The description of the type or name of the antibiotic substance is a duplicate of the foregoing description of an air cleaning filter and, thus, is referenced, rather than repeated.

The antibiotic composite solution may contain the binder in 0.001 to 30 weight % based on the entire antibiotic composite solution, may contain the binder in 0.01 to 20 weight %, and may contain the binder in 0.1 to 7 weight %. The description of the type or name of the binder is a duplicate of the foregoing description of an air cleaning filter and, thus, is referenced, rather than repeated.

The antibiotic composite solution may further include a metal, and the metal may include any one of Ag, Cu, Zn, Ca, Mn and their combinations, or may be in the form of a metal sol.

The antibiotic composite solution may be a coating solution composed of 1 to 10 volume % of the ginseng extract solution, 0.05 to 1 volume % of the antibiotic substance, 1 to 10 volume % of the metal sol, and 79 to 93 volume % of a binder solvent mixed with a binder and a second solvent. When the coating solution is applied to the antibiotic composite solution, the mixture and coating properties of the coating solution may be enhanced.

The ginseng extract powder in 1 to 20 weight % may be mixed and agitated with the first solvent to produce the ginseng extract solution.

The binder solvent may contain the binder and second solvent in 20 to 30 volume % and 70 to 80 volume %, respectively, and the second solvent may be any one of water (pure), ethanol, and their combinations.

The antibiotic composite solution or coating solution may be impregnated or coated on a supporting material, and a known coating method may be properly applied to the impregnation or coating method. For instance, a dipping method, a roll method, a spray method, and the like may be applicable thereto.

When the antibiotic composite solution or the coating solution is impregnated or coated on the supporting material, it may further include a suitable drying process.

The method of manufacturing an air cleaning filter may include a ginseng extract, and, thus, may be effective in removing or sterilizing microbes, thereby providing antibiotic and sterilization functions in addition to an air cleaning function as well as providing a method of manufacturing an air cleaning filter which is non-hazardous to the human body.

The air cleaning filter may be applicable to any place where the air cleaning filter is needed, and used for an air cleaning device. In particular, using the characteristics of non-hazardousness to human body and excellent antibiotic and sterilization performance, it may be used as an air cleaning filter for air cleaning at an inner portion of the refrigerator or kimchi refrigerator and microbe propagation prevention. Furthermore, the air cleaning filter may be used for household appliances, such as an air conditioner, an air cleaner, a styler, and the like or an automobile air conditioner for circulating indoor air, or may be used as a filter such as a deodorizing filter, HEPA filter, and the like, or may be used together with them.

Production Example

Extract Production Step—Production of Ginseng Extract

Ginseng rootlets and ginseng leaves are crushed using a homogenizer to produce a ginseng extract (crushing process).

30 g of the crushed ginseng material and 600 ml of distilled water are mixed to produce a mixture, and the mixture is sterilized at 121° C. for 15 minutes using a high pressure steam sterilizer (sterilization process), and the sterilized mixture is cold-discharged to produce a sterile crushed ginseng material (first fermentation process).

One percent of a culture fluid containing *lactobacillus plantarum* (*L. plantarum*) is added to the crushed ginseng material based on 100 ml of the sterile crushed ginseng material to produce a ginseng culture fluid (second fermentation process). The ginseng culture fluid is fermented at 35° C. for 48 hours using a shaking incubator to produce a fermented mixture (third fermentation process)

600 ml of the mixture is mixed with 6 L of methanol, and agitated and extracted from the material three times for 3 hours to produce a ginseng extract, and filtered out to produce a ginseng extract (extraction process).

The ginseng extract is vacuum-concentrated using a rotary vacuum evaporator and a 45° C. water bath, and pulverized to produce a ginseng extract powder (pulverization process).

The ginseng extract powder is used as a ginseng extract in the following example.

Experiment Example

Evaluation of Sterile Performance of Ginseng Extract, Antibiotic Substance and Binder 1. Measurement of Minimal Inhibitory Concentration (MIC)

Polyvinylpyrrolidone iodine (hereinafter, abbreviated as "PVPI"), phthalaldehyde (hereinafter, abbreviated as "PA"), potassium disulphite (hereinafter, abbreviated as "PD") bronopol, norspermidine (hereinafter, abbreviated as "NS), and the ginseng extract were sequentially diluted, respectively, and prepared with various concentrations to prepare MIC measurement specimens. About $10^{4-5}$ cfu/ml of *escherichia coli* (*E. coli*) and about $10^{4-5}$ cfu/ml of *staphylococcus aureus* (*S. aureus*) were added to the MIC measurement specimens, respectively. The specimens were cultured at 35° C. for 14-16 hours and then the turbidity was examined, respectively.

As a comparative example, specimens to which the *E. coli* and the *S. aureus* were added to distilled water, respectively, were cultured at the same time, and the minimal inhibitory concentration of the specimens was measured with reference to specimens subsequent to the culture and the turbidity of the comparative example subsequent to the culture. The measured minimal inhibitory concentration of the relevant microbes for each material is illustrated in the following Table 1.

TABLE 1

| Name | *E. coli* | *S. aureus* |
| --- | --- | --- |
| PVPI | 1.875% | 1.875% |
| Ginseng extract | 0.625% | 0.312% |
| Bronopol | Less than 0.0009% | Less than 0.0009% |
| PA | 0.156% | 0.156% |
| NS | 0.312% | 0.078% |
| PD | 0.156% | 0.078% |

(Note)
The above percent (%) denotes weight %.

Referring to the Table 1, all the ginseng extract, antibiotic substance and antibiotic binder exhibited an excellent microbial growth inhibition effect, and thus it was confirmed that all the materials has an antibiotic effect.

2. Paper Disc Experiment $10^5$ cfu/ml of *E. coli* and *S. aureus* were sub-cultured in a Mueller Hinton agar, respectively, and then smeared.

PVPI, ginseng extract, bronopol, PA, NS and PD were introduced to the paper disc, respectively, and left and dried for 5 to 10 minutes. The dried paper disc was put on a culture medium smeared with the *E. coli* and *S. aureus* with a sufficient interval, and cultured for 24 hours in a 35° C. incubator and then the size of clear zone was examined and the result is summarized in the following Table 2.

TABLE 2

| | | *E. coli* | | *S. aureus* | |
| --- | --- | --- | --- | --- | --- |
| Name | Concentration* | MIC value* | clear zone (mm) | MIC value* | clear zone (mm) |
| PVPI | 0.9375% | 1.875% | 12 | 1.875% | 30 |
| Ginseng extract | 1.25% | 0.625% | 6 | 0.312% | 13 |
| PA | 0.156% | Less than 0.0009% | 10 | Less than 0.0009% | 11 |
| Bronopol | 0.0312% | 0.156% | 10 | 0.156% | 10 |
| NS | 1.25% | 0.312% | 14 | 0.078% | 23 |
| PD | 0.625% | 0.156% | 12 | 0.078% | 32 |

The value indicated by the asterisk (*) denotes concentration (weight %).

Referring to the Table 2, a clear zone against both the *E. coli* and *S. aureus* was formed for all the ginseng extract, antibiotic substance and antibiotic binder, and thus it was confirmed that all the materials have an antibiotic effect, and it was also confirmed that the antibiotic effect on *S. aureus* is more effective.

3. Experiment Using Shaking Flask Method

A maintenance medium produced with 1% of nutrient broth and 0.5% of NaCl and inoculated with about $10^5$ cfu/ml of *E. coli* was prepared. Materials of PVPI, ginseng extract, bronopol, PA and NS were introduced to the medium, respectively, and reacted at 35° C., and the antibiotic effect was examined using a pour plate method after 6 hours and 24 hours had been passed.

The concentration of the above materials and their antibiotic effects are summarized in the following Table 3.

TABLE 3

| Name | Concentration (wt %) | MIC value of *E. coli* (wt %) | Antibiotic effect after 6 hours | Antibiotic effect after 24 hours |
| --- | --- | --- | --- | --- |
| PVPI | 0.75% | 1.875% | 99.99% | 100% |
| Ginseng extract | 0.625% | 0.625% | 99.99% | 100% |
| PA | 0.125% | Less than 0.0009% | 99.99% | 100% |
| Bronopol | 0.0625% | 0.156% | 99.99% | 100% |
| NS | 0.125% | 0.312% | 99.99% | 100% |

The antibiotic effect in the Table 3 was calculated using the following equation.

$$\text{Antibiotic effect } (\%) = \left(\frac{Mc - Me}{Mc}\right) \times 100$$

Me: Cell number of maintenance medium to which each material is added
Mc: Cell number of maintenance medium to which each material is not added Referring to the Table 3, it was confirmed that all the above materials exhibit an antibiotic effect, and the ginseng extract also exhibits an antibiotic effect similar to that of the antibiotic substance or antibiotic binder.

Example

Manufacture of Air Cleaning Filter and Evaluation of the Sterilization Performance 1. Manufacture of Air Cleaning Filter Using Non-Woven Polypropylene (PP) Fabric as a Supporting Material and Evaluation of the Sterilization Performance
1) Manufacture of Air Cleaning Filter
An air cleaning filter was manufactured using non-woven polypropylene (PP) fabric as a supporting material. The produced ginseng extract was used, and mixed with the antibiotic substance and antibiotic binder disclosed in the following Table 4 at each concentration to produce antibiotic composite solutions of the examples 1 through 7, respectively (solution production process). In all the examples, distilled water was used as a solvent.

TABLE 4

|  | *Ginseng* extract concentration | Type of antibiotic substance (concentration) | Antibiotic binder (concentration) | Amount of substance |
|---|---|---|---|---|
| Example 1 | 0.5% | Bronopol (0.1%) | PVPI (5%) | 0.113 g |
| Example 2 | 0.3% | Bronopol (0.05%), PA (0.05%) | PVPI (3%) | 0.067 g |
| Example 3 | 0.3% | Bronopol (0.05%), PA (0.05%) | PVPI (2%) | 0.040 g |
| Example 4 | 0.3% | Bronopol (0.05%), PA (0.05%) | PVPI (1%) | 0.017 g |
| Example 5 | 0.3% | Bronopol (0.05%) | Norspermidine (3%) | 0.039 g |
| Example 6 | 0.3% | Bronopol (0.1%) | Norspermidine (3%) | 0.057 g |
| Example 7 | 0.5% | Bronopol (0.1%) | Norspermidine (1%) | 0.025 g |

*In the above Table 4, all the percents (%) indicating concentration denote weight % (wt %), and the amount of substance denotes the weight of the antibiotic composite solution coated on the non-woven fabric.

The antibiotic composite solution of the examples 1 through 7 was coated on a supporting material, respectively, to produce the air cleaning filter samples of the examples 1 through 7 (fixation process).

The antibiotic effect was measured using the samples of the examples 1 through 7 in a similar manner to the shaking flask method. *E. coli* was used as a test strain, and left for 1 hour, 6 hours, and 24 hours, respectively, and then the antibiotic effect was calculated in a similar manner to Table 3, and the result is shown in the following Table 5.

TABLE 5

|  | Reaction time 1 hour | Reaction time 6 hours | Reaction time 24 hours |
|---|---|---|---|
| Example 1 | 100% | 100% | 100% |
| Example 2 | 100% | 100% | 100% |
| Example 3 | 96.00% | 99.99% | 100% |
| Example 4 | 46.67% | 99.99% | 100% |
| Example 5 | — | — | 50.00% |
| Example 6 | — | — | 53.85% |
| Example 7 | — | — | 32.14% |

*In the above Table 5, the mark (—) denotes that the antibiotic effect was not measured.

Referring to the Table 5, all the examples 1 through 7 exhibited an antibiotic effect, and the cases of the examples 1 through 4 to which PVPI was applied as an antibiotic binder exhibited more antibiotic effect than those of the examples 5 through 7 to which norspermidine (NS) was applied as an antibiotic binder.

2. Manufacture of Air Cleaning Filter Example One Using Zebra Filter (Supporting Material) and Evaluation of Sterilization Performance Thereof 1) Manufacture of Air Cleaning Filter Example One Air cleaning filter example one was manufactured using a zebra filter (made by Lyusen) as a supporting material. The produced ginseng extract was used, and mixed with the antibiotic substance and antibiotic binder disclosed in the following Table 6 at each concentration to produce antibiotic composite solutions of the examples 8 through 10, respectively (solution production process). In all the examples, distilled water was used as a solvent.

TABLE 6

|  | *Ginseng* extract concentration | Type of antibiotic substance (concentration) | Antibiotic binder (concentration) | Amount of substance |
|---|---|---|---|---|
| Example 8 | 0.3% | Bronopol (0.05%), PA (0.05%) | PVPI (5%) | 0.031 g |
| Example 9 | 0.3% | Bronopol (0.05%), PA (0.05%) | PVPI (4%) | 0.033 g |
| Example 10 | 0.3% | Bronopol (0.05%), PA (0.05%) | PVPI (3%) | 0.007 g |

*In the above Table 6, all the percents (%) indicating concentration denote weight % (wt %), and the amount of substance denotes the weight of the antibiotic composite solution coated on the non-woven fabric.

The antibiotic composite solution of the examples 8 through 10 was coated on a supporting material, respectively, to produce the air cleaning filter samples of the examples 8 through 10 (fixation process).

2) Evaluation of Antibiotic Performance

The antibiotic effect was measured using the samples of the examples 8 through 10 in a similar manner to the shaking flask method. *E. coli* was used as a test strain, and left for 1 hour, 6 hours, and 24 hours, respectively, and then the antibiotic effect was calculated in a similar manner to Table 3, and the result is shown in the following Table 7.

TABLE 7

|  | Reaction time 1 hour | Reaction time 6 hours | Reaction time 24 hours |
|---|---|---|---|
| Embodiment 8 | 100% | 100% | 100% |
| Embodiment 9 | 100% | 100% | 100% |
| Embodiment 10 | 99.99% | 99.99% | 100% |

Referring to Table 7, all the examples 8 through 10 exhibited an antibiotic effect against the test strain, and also exhibited an antibiotic effect even after coating on the supporting material, and thus it was confirmed that the air cleaning filter example one performs as an air cleaning filter.

3) Evaluation of the Virus Removal Performance of the Filter Against Feline Calicivirus (FCV)

The air cleaning filter example one was left in a reaction temperature and reaction time condition to evaluate the virus removal performance of the air cleaning filter example one.

The antivirus performance was evaluated using feline calcivirus (FCV F9 strain, cat. #VR-782-ATCC) having similar genetic structure and physicochemical property to norovirus and belonging to the same caliciviridae group.

Whether or not it was infected based on the virus reaction time was checked using feline calcivirus (FCV F9 strain, cat. #VR-782-ATCC) to confirm the virus removal effect.

Eagle's Minimum Essential Medium MEM (10% FBS or HS) was placed on a 75 cm² cell culture flask, and cultured for one night in a 37° C., 5% CO2 incubator. Cells was sub-cultured every two days, and the FCV F9 strain was inoculated to prepare cells and viruses by checking whether the viruses were cultured on the prepared specimen while culturing them in the 37° C., 5% CO2 incubator.

$1.3*10^4/100$ μl of CrFK cells were sub-cultured in each well using a 96-well cell culture plate, and cultured for one night in the 37° C., 5% CO2 incubator.

Next day, the prepared viruses were decimally diluted on a maintenance medium. A growth medium was removed using an aspirator on a 96-well plate, and then the diluted viruses were inoculated in eight wells for each 25 μl.

Viruses were infected for 90 minutes in the 37° C., 5% CO2 incubator, and then 100 μl of the maintenance medium was added to each well. Virus titer was determined by reacting viruses with the extract for a predetermined period of time and then comparing the remaining amount of viruses with the control group and calculating the tissue culture infectious dose (TCID) 50 measured on CrFK cells.

On the fifth day of virus culture, cells dissolved by viruses were visualized and then the dilution stage of the well showing a cytopathic effect (CPE) by more than 50% was assessed using the Reed-Munch method, and displayed on Log TCID50. The result is shown in the following Table 8.

Referring to Table 8, it was also confirmed that antibiotic performance against viruses occurred. In particular, it was confirmed that an antibiotic effect greater than 99% was shown even in the low temperature environment, such as a refrigerator.

3. Manufacture of Air Cleaning Filter Example One Using Zebra Filter (Supporting Material) and Evaluation of Sterilization Effect Thereof by Species 1) Example of Manufacture Air cleaning filter example two was manufactured using a zebra filter (made by Lyusen) as a supporting material. The produced ginseng extract was used, and mixed with the antibiotic substance, antibiotic binder and metal sol disclosed in the following Table 9 at each concentration to produce antibiotic composite solutions of the example 11, respectively (solution production process).

[FIG. 9]

|  | Ginseng extract solution[1] | Type of antibiotic substance (concentration) | Binder[2] (concentration) | Metal sol content | Solvent |
|---|---|---|---|---|---|
| Example 11 | 5% | Glutaraldehyde (1%) | Binder resin (25%) | 8% | Pure water (remaining) |

In the above Table 9, all the percents (%) indicating concentration denote volume % (vol %).
[1]The *ginseng* extract solution is a solution mixed with the ginseng extract powder (10 weight %), water (pure, 70 weight %), and ethanol (20 weight %).
[2]The binder resin is a silicone-modified epoxy resin produced by 10% of epoxy resin and 90% of silicone resin.

The antibiotic composite solution of the example 11 was coated on the supporting material, respectively, to produce the samples of the air cleaning filter example one in examples 11-1 through 11-23, and examples 11-31 through 11-40 (fixation process).

2) Evaluation of Antibiotic Effects by Species (35° C.)

The evaluation of antibiotic effects with *escherichia coli, staphylococcus aureus, salmonella typhimurium*, and *listeria monocytogenes* as experimental strains, respectively, was carried out using the samples of the manufacturing example 3-1).

The evaluation of antibiotic effects was repeatedly carried out for each strain, and tested by the method of ASTM E2149-10, and maintained at 35° C. for a reaction time and then the antibiotic effects were calculated, and the result is shown in the following Table 10.

TABLE 8

|  |  | Reaction time | | | | |
|---|---|---|---|---|---|---|
|  |  | 15 min | 30 min | 60 min | 3 hr | 5 hr |
| 35° C. | Control | | 6.1 ($1.3 \times 10^6$) | | | |
|  | Treated group | 2.9 ($7.9 \times 10^2$) | ND | ND | — | — |
|  | Reduction rate | 99.94% | 100% | 100% | — | — |

|  |  | Reaction time | | | | |
|---|---|---|---|---|---|---|
|  |  | — | 30 min | 60 min | 3 hr | 5 hr |
| 3° C. | Control | | 5.9 ($7.9 \times 10^5$) | | | |
|  | Treated group | — | 3.6 ($4.0 \times 10^3$) | 3.1 ($1.3 \times 10^3$) | 3.1 ($1.3 \times 10^3$) | 3.1 ($1.3 \times 10^3$) |
|  | Reduction rate | — | 99.49% | 99.84% | 99.84% | 99.84% |

(Unit: TCID50/mL)

TABLE 10

Experimental strain-temperature
*Escherichia coli* - 35° C.

| Reaction time | | 11-1 | 11-2 | 11-3 | 11-4 | 11-5 | 11-6 | 11-7 | 11-8 |
|---|---|---|---|---|---|---|---|---|---|
| | Control | $2.1 \times 10^5$ | $2.7 \times 10^5$ | $1.4 \times 10^5$ | $5.4 \times 10^5$ | $5.4 \times 10^5$ | $4.1 \times 10^5$ | $2.2 \times 10^5$ | $5.0 \times 10^5$ |
| 30 min | Cell number | $5.4 \times 10^2$ | $7.2 \times 10^2$ | ND | ND | ND | ND | ND | ND |
| | Reduction rate | 99.74% | 99.73% | 100% | 100% | 100% | 100% | 100% | 100% |
| 60 min | Cell number | ND | ND | ND | ND | ND | ND | ND | ND |
| | Reduction rate | 100% | 100% | 100% | 100% | 100% | 100% | 100% | 100% |

Experimental strain-temperature
*Staphylococcus aureus* - 35° C.

| Reaction time | | 11-8 | 11-9 | 11-10 | 11-11 | 11-12 | 11-13 | — | — |
|---|---|---|---|---|---|---|---|---|---|
| | Control | $4.2 \times 10^5$ | $5.4 \times 10^5$ | $2.7 \times 10^5$ | $5.3 \times 10^5$ | $5.9 \times 10^5$ | $3.3 \times 10^5$ | — | — |
| 30 min | Cell number | ND | ND | ND | ND | ND | ND | — | — |
| | Reduction rate | 100% | 100% | 100% | 100% | 100% | 100% | — | — |
| 60 min | Cell number | ND | ND | ND | ND | ND | ND | — | — |
| | Reduction rate | 100% | 100% | 100% | 100% | 100% | 100% | — | — |

Experimental strain-temperature
*Salmonella typhimurium* - 35° C.

| Reaction time | | 11-14 | 11-15 | 11-16 | 11-17 | 11-18 | — | — | — |
|---|---|---|---|---|---|---|---|---|---|
| | Control | $2.6 \times 10^5$ | $1.7 \times 10^5$ | $2.1 \times 10^5$ | $2.2 \times 10^5$ | $2.0 \times 10^5$ | — | — | — |
| 30 min | Cell number | ND | 20 | $8.0 \times 10^3$ | ND | ND | — | — | — |
| | Reduction rate | 100% | 99.99% | 96.19% | 100% | 100% | — | — | — |
| 60 min | Cell number | ND | ND | ND | ND | ND | — | — | — |
| | Reduction rate | 100% | 100% | 100% | 100% | 100% | — | — | — |

Experimental strain-temperature
*Listeria monocytogenes* - 35° C.

| Reaction time | | 11-19 | 11-20 | 11-21 | 11-22 | 11-23 | — | — | — |
|---|---|---|---|---|---|---|---|---|---|
| | Control | $1.6 \times 10^5$ | $4.5 \times 10^5$ | $3.3 \times 10^5$ | $4.3 \times 10^5$ | $2.6 \times 10^5$ | — | — | — |
| 30 min | Cell number | ND | $2.1 \times 10^4$ | ND | ND | ND | — | — | — |
| | Reduction rate | 100% | 95.33% | 100% | 100% | 100% | — | — | — |
| 60 min | Cell number | ND | ND | ND | ND | ND | — | — | — |
| | Reduction rate | 100% | 100% | 100% | 100% | 100% | — | — | — |

*The symbol "ND" in the above Table denotes that microbes were not detected.

Referring to Table 10, all the examples 11-1 through 11-23 have an antibiotic effect against each experimental strain. In particular, the result confirms that the antibiotic effects have an effect on various types of strains as well as specific types of strains, and exhibits that, although the strain concentration is changed to some extent, almost 100% of strain reduction rates are shown after 60 minutes has passed, thereby having antibiotic effects.

3) Evaluation of Antibiotic Effects by Species (3° C.)

The evaluation of antibiotic effects at 3° C. with *escherichia coli*, *staphylococcus aureus*, *salmonella typhimurium*, and *listeria monocytogenes* as experimental strains, respectively, was carried out using the samples of the manufacturing example 3-1).

The evaluation of antibiotic effects was repeatedly carried out for each strain, and tested by the method of 3° C. ASTM E2149-10, and left at 3° C. for a reaction time and then the antibiotic effects were calculated, and the result is shown in the following Table 11.

TABLE 11

| | | Experimental strain-temperature Escherichia coli-3° C. | | |
|---|---|---|---|---|
| Reaction time | | 11-31 | 11-32 | 11-33 |
| 30 min | Control | $3.6 \times 10^5$ | $3.3 \times 10^5$ | $5.9 \times 10^5$ |
| | Cell number | Exp X | $4.0 \times 10^3$ | $2.6 \times 10^3$ |
| | Reduction rate | — | 99.79% | 99.56% |
| 1 hr | Cell number | $2.8 \times 10^4$ | $1.4 \times 10^3$ | $1.2 \times 10^3$ |
| | Reduction rate | 92.22% | 99.58% | 99.80% |
| 3 hr | Cell number | Exp X | ND | ND |
| | Reduction rate | — | 100% | 100% |
| 5 hr | Cell number | $3.8 \times 10^2$ | ND | ND |
| | Reduction rate | 99.90% | 100% | 100% |

| | | Experimental strain-temperature Staphylococcus aureus-3° C. | | |
|---|---|---|---|---|
| Reaction time | | 11-34 | 11-35 | — |
| 30 min | Control | $4.7 \times 10^5$ | $4.5 \times 10^5$ | — |
| | Cell number | $3.6 \times 10^5$ | $2.7 \times 10^5$ | — |
| | Reduction rate | 23.40% | 40.00% | — |
| 1 hr | Cell number | $2.6 \times 10^5$ | $2.4 \times 10^5$ | — |
| | Reduction rate | 44.68% | 44.67% | — |
| 3 hr | Cell number | $1.1 \times 10^5$ | $9.0 \times 10^4$ | — |
| | Reduction rate | 76.60% | 80.00% | — |
| 5 hr | Cell number | $9.7 \times 10^4$ | $3.7 \times 10^4$ | — |
| | Reduction rate | 79.36% | 91.78% | — |

| | | Experimental strain-temperature Salmonella typhimurium-3° C. | | |
|---|---|---|---|---|
| Reaction time | | 11-36 | 11-37 | 11-38 |
| 30 min | Control | $4.1 \times 10^5$ | $2.6 \times 10^5$ | $2.6 \times 10^5$ |
| | Cell number | $3.5 \times 10^5$ | $1.3 \times 10^5$ | $3.9 \times 10^5$ |
| | Reduction rate | 14.63% | 50.00% | 85.00% |
| 1 hr | Cell number | $2.6 \times 10^5$ | $6.4 \times 10^4$ | $2.3 \times 10^4$ |
| | Reduction rate | 36.59% | 75.38% | 91.15% |
| 3 hr | Cell number | $5.5 \times 10^4$ | $4.1 \times 10^4$ | $1.2 \times 10^4$ |
| | Reduction rate | 86.59% | 84.23% | 95.39% |
| 5 hr | Cell number | $1.5 \times 10^4$ | $1.2 \times 10^4$ | $3.0 \times 10^3$ |
| | Reduction rate | 96.34% | 95.38% | 98.85% |

| | | Experimental strain-temperature Listeria monocytogenes-3° C. | | |
|---|---|---|---|---|
| Reaction time | | 11-39 | 11-40 | — |
| 30 min | Control | $4.0 \times 10^5$ | $3.3 \times 10^5$ | — |
| | Cell number | $4.8 \times 10^4$ | $1.6 \times 10^5$ | — |
| | Reduction rate | 88.00% | 51.52% | — |
| 1 hr | Cell number | $4.4 \times 10^4$ | $1.4 \times 10^5$ | — |
| | Reduction rate | 89.00% | 57.58% | — |
| 3 hr | Cell number | $2.0 \times 10^4$ | $5.5 \times 10^4$ | — |
| | Reduction rate | 95.00% | 83.33% | — |
| 5 hr | Cell number | $9.2 \times 10^3$ | $1.6 \times 10^4$ | — |
| | Reduction rate | 97.70% | 95.15% | — |

*The symbol "ND" in the above Table denotes that microbes were not detected.

In the above Table 11, it was confirmed that the result of evaluating antibiotic effects with each experimental strain at 3° C. was effective. In particular, it is confirmed that the experimental result for *E. coli* was 99.9% through 100.00% and thus microbes were almost sterilized in case of the reaction time of 5 hours, and the results for other strains also exhibited an excellent antibiotic effects in the range of about 80% and about 99%. Referring to Table 10, it was confirmed that a sterile filter exhibits an antibiotic characteristic for various strains even in the low temperature environment, such as a refrigerator.

Although some implementations of the present disclosure have been described in detail, the scope of the present disclosure is not limited to the described implementations. Various modifications and improvements thereto may be made by those skilled in the art using the basic concept of the present disclosure.

What is claimed is:

1. An air cleaning filter unit, comprising:
   a first filter that comprises:
      a lactic-acid fermented ginseng extract;
      a supporting material configured to filter air flowing through the air cleaning filter unit;
   a binder configured to bind the ginseng extract to the supporting material; and
      wherein the binder comprises at least one of polyvinylpyrrolidone iodine (PVPI) and silicone-modified resin; and
   a second filter, a third filter, and a fourth filter, wherein a mesh size of the second filter, the third filter, and the fourth filter sequentially disposed from an air suction port toward an air discharge port is decreased from the second filter to the fourth filter.

2. The air cleaning filter unit of claim 1, wherein the silicone-modified resin comprises at least one of silicone-modified acrylic resin, silicone-modified urethane resin, silicone-modified epoxy resin, and silicone-modified vinyl resin.

3. The air cleaning filter unit of claim 1, wherein the lactic-acid fermented ginseng extract comprises at least one of a lactic-acid fermented ginseng leaf extract, a lactic-acid fermented ginseng rootlet extract, and a lactic-acid fermented ginseng main root extract.

4. The air cleaning filter unit of claim 1, wherein the lactic-acid fermented ginseng extract comprises at least one of a lactic-acid fermented extract solution of ginseng, a concentrated lactic-acid fermented extract solution of ginseng, and a dried lactic-acid fermented extract solution of ginseng.

5. The air cleaning filter unit of claim 1, wherein the supporting material comprises at least one of a non-woven fabric, a paper fiber, a glass fiber, an ion-exchange fiber, a cellulose fiber, an asbestos fiber, activated carbon, titanium dioxide, zinc, copper, and aluminium.

6. The air cleaning filter unit of claim 1, wherein the first filter further comprises a metal.

7. An air cleaning filter unit comprising:
   a first filter that comprises:
      a ginseng extract;
      a supporting material configured to filter air flowing through the air cleaning filter unit;
      a binder configured to bind the ginseng extract to the supporting material; and
      an antibiotic substance having sterilization and antibiotic functions,
      wherein the antibiotic substance comprises at least one of phthalaldehyde (PA), potassium disulphite (PD), bronopol, sodium desoxycholate, glutaraldehyde, sodium desoxycholate, and quaternary ammonium; and
   a second filter, a third filter, and a fourth filter, wherein a mesh size of the second filter, the third filter, and the fourth filter sequentially disposed from an air suction port toward an air discharge port is decreased from the second filter to the fourth filter.

8. The air cleaning filter unit of claim 7, wherein the antibiotic substance comprises at least one of phthalaldehyde (PA), bronopol, and glutaraldehyde.

9. The air cleaning filter unit of claim 7, wherein the supporting material is impregnated or coated with an antibiotic composite that includes the lactic-acid fermented ginseng extract, the antibiotic substance, and the binder.

10. The air cleaning filter unit of claim 7, wherein a weight ratio of a sum of the lactic-acid fermented ginseng extract and the antibiotic substance, and the antibiotic binder is 1:2 to 1:80.

11. A filter module, comprising:
a housing that defines an air suction port and an air discharge port;
an air cleaning filter unit disposed within the housing and that comprises:
a first filter, a second filter, and a third filter, wherein a mesh size of the first filter, the second filter, and the third filter sequentially located from the air suction port toward the air discharge port decreases from the first filter to the third filter; and
a lactic-acid fermented ginseng extract and a binder that binds the lactic-acid fermented ginseng extract to a fourth filter; and
a blower fan,
wherein the binder comprises at least one of polyvinylpyrrolidone iodine (PVPI) and silicone-modified resin.

12. The filter module of claim 11, wherein the air cleaning filter unit further comprises an antibiotic substance, a metal, and a coating layer that is coated on the fourth filter and that includes the lactic-acid fermented ginseng extract and the binder.

13. The filter module of claim 11, wherein the air cleaning filter unit is coupled to the housing in an integrated or detachable structure.

14. A refrigerator, comprising:
a main body provided with a storage space for refrigerated storage;
a compressor provided within the main body to compress refrigerant;
one or more doors configured to selectively open or close the storage space; and
a filter module of claim 11 mounted within the storage space.

15. The refrigerator of claim 14, wherein the main body comprises:
an inner case defining the storage space;
an outer case defining an external appearance of the refrigerator;
a cool air duct positioned in a space between the inner case and the outer case and configured to supply cool air; and
a multi duct positioned in a space between the inner case and the outer case and having one or more discharge ports that receive sterile air discharged from the filter module and deliver the received sterile air to the storage space.

16. The refrigerator of claim 14, further comprising:
a controller configured to control operation of the filter module.

17. A method of manufacturing an air cleaning filter unit, the method comprising:
producing a lactic-acid fermented ginseng extract by:
preparing crushed ginseng material by crushing at least one of ginseng rootlets, ginseng leaves, and ginseng main roots;
sterilizing a mixture produced by mixing the crushed ginseng material with a solvent;
fermenting the sterilized mixture using *Lactobacillus*; and
preparing a raw lactic-acid fermented ginseng extract solution by mixing the mixture with alcohol;
preparing an antibiotic composite solution by mixing a composite comprising the lactic-acid fermented ginseng extract, an antibiotic binder, and a solvent;
fixing the antibiotic composite solution to a first filter; and
combining the first filter with a second filter, a third filter, and a fourth filter, wherein a mesh size of the second filter, the third filter, and the fourth filter sequentially disposed from an air suction port toward an air discharge port is decreased from the second filter to the fourth filter,
wherein the antibiotic binder comprises at least one of polyvinylpyrrolidone iodine (PVPI) and silicone-modified resin.

18. The method of claim 17, wherein fermenting the sterilized mixture using *Lactobacillus* comprises:
preparing a sterile crushed ginseng material by cooling the sterilized mixture;
preparing a ginseng culture fluid by adding a culture fluid comprising *Lactobacillus* to the sterile crushed ginseng material; and
preparing a lactic-acid fermented mixture by fermenting the ginseng culture fluid.

19. The method of claim 18, wherein preparing the lactic-acid fermented mixture by fermenting the ginseng culture fluid is carried out at temperatures of 25 to 35° C. for 0.5 to 3 days.

20. The method of claim 17, further comprising concentrating and pulverizing the raw lactic-acid fermented ginseng extract solution to produce a lactic-acid fermented ginseng extract power.

21. The method of claim 18, wherein the culture fluid further comprises at least one of *lactobacillus plantarum* (*L. plantarum*), *candida utilis* (*C. utilis*), and *aspergillus oryza* (*A. oryzae*).

22. The method of claim 17, wherein the antibiotic composite solution comprises the lactic-acid fermented ginseng extract powder in a weight ratio of 0.001 to 30 weight percentage.

23. The method of claim 17, wherein the antibiotic composite solution further comprises a metal.

* * * * *